United States Patent
Wahrenberg et al.

(10) Patent No.: US 11,954,785 B2
(45) Date of Patent: Apr. 9, 2024

(54) DATA PROCESSING METHOD AND APPARATUS

(71) Applicant: CANON MEDICAL SYSTEMS CORPORATION, Otawara (JP)

(72) Inventors: Magnus Fredrik Wahrenberg, Edinburgh (GB); Steven Reynolds, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 52 days.

(21) Appl. No.: 17/643,031

(22) Filed: Dec. 7, 2021

(65) Prior Publication Data
US 2023/0177760 A1    Jun. 8, 2023

(51) Int. Cl.
| | |
|---|---|
| G06T 15/00 | (2011.01) |
| G06F 16/51 | (2019.01) |
| G06T 1/60 | (2006.01) |
| G06T 15/08 | (2011.01) |
| G06T 15/50 | (2011.01) |
| G16H 30/40 | (2018.01) |

(52) U.S. Cl.
CPC .......... *G06T 15/005* (2013.01); *G06F 16/51* (2019.01); *G06T 1/60* (2013.01); *G06T 15/08* (2013.01); *G06T 15/506* (2013.01); *G16H 30/40* (2018.01); *G06T 2210/41* (2013.01)

(58) Field of Classification Search
CPC ......... G06T 15/005; G06T 1/60; G06T 15/08; G06T 15/506; G06T 2210/41; G16H 30/40; G06F 16/51
See application file for complete search history.

(56) References Cited

U.S. PATENT DOCUMENTS

| | | | |
|---|---|---|---|
| 11,080,111 B1 * | 8/2021 | Perelygin | G06F 9/544 |
| 11,605,147 B2 * | 3/2023 | Kalele | G06T 1/60 |
| 2014/0232719 A1 | 8/2014 | Wahrenberg | |

(Continued)

FOREIGN PATENT DOCUMENTS

CN    107811706 A    3/2018

OTHER PUBLICATIONS

González, Marc, and Enric Morancho. "Multi-GPU systems and Unified Virtual Memory for scientific applications: The case of the NAS multi-zone parallel benchmarks." Journal of Parallel and Distributed Computing 158 (2021): 138-150. (Year: 2021).*

(Continued)

*Primary Examiner* — Xin Sheng
(74) *Attorney, Agent, or Firm* — Oblon, McClelland, Maier & Neustadt, L.L.P.

(57) ABSTRACT

A medical image processing apparatus for rendering medical images includes a first GPU and a second GPU, each configured to read from and write to a data structure stored in virtual memory. The data structure is configured to be read by both the first GPU and the second GPU and the data structure is configured such that the first GPU can write to a first sub-space of the data structure and the second GPU can write to a second sub-space of the data structure. The first sub-space and the second sub-space are independent. The first GPU is configured to write data relating to preprocessing for rendering to the first sub-space and the second GPU is configured to read the written data and to render at least one image based on the written data.

18 Claims, 7 Drawing Sheets

(56) References Cited

U.S. PATENT DOCUMENTS

| | | |
|---|---|---|
| 2014/0375662 A1* | 12/2014 | Chen .................. G06T 1/60 |
| | | 345/542 |
| 2016/0217563 A1 | 7/2016 | Wahrenberg |
| 2016/0292913 A1 | 10/2016 | Wahrenberg |
| 2017/0365051 A1 | 12/2017 | Wahrenberg et al. |
| 2018/0174355 A1 | 6/2018 | Day et al. |
| 2019/0029526 A1 | 1/2019 | Hashizume |
| 2019/0122636 A1* | 4/2019 | Tang .................. G09G 5/10 |
| 2019/0311530 A1 | 10/2019 | Wahrenberg |
| 2020/0064470 A1 | 2/2020 | Qin |
| 2021/0287426 A1* | 9/2021 | Wyman .............. G06T 15/005 |

OTHER PUBLICATIONS

Jaroš, Milan, et al. "GPU accelerated path tracing of massive scenes." ACM Transactions on Graphics (TOG) 40.2 (2021): 1-17. (Year: 2021).*

Christensen, Cameron, et al. "Topology-aware image compositing using NVLink." 2016 IEEE 6th Symposium on Large Data Analysis and Visualization (LDAV). IEEE, 2016. (Year: 2016).*

Xie, Chenhao, et al. "OO-VR: Numa friendly object-oriented VR rendering framework for future NUMA-based multi-GPU systems." 2019 ACM/IEEE 46th Annual International Symposium on Computer Architecture (ISCA). IEEE, 2019. (Year: 2019).*

M. Harris "Unified Memory for CUDA beginners", https://developer.nvidia.com/blog/unified-memory-cuda-beginners/ Jun. 19, 2017; (6 pages).

* cited by examiner

DATA PROCESSING METHOD AND APPARATUS

FIELD

Embodiments described herein relate generally to a method of, and apparatus for processing data, for example processing data using one or more graphics processing units (GPUs).

BACKGROUND

It is known to render images from volumetric imaging data, for example from volumetric medical imaging data. A set of volumetric imaging data may be referred to as an image volume. The set of volumetric imaging data may comprise a plurality of voxels with associated voxel values, with each voxel being representative of a corresponding spatial location in a medical imaging scan. For example, in the case of computed tomography (CT) data, the voxel value associated with each voxel may be a voxel intensity value that is representative of an attenuation of applied X-ray radiation at the location represented by the voxel.

It is known to render three-dimensional (3D) imaging data to produce a rendered image that appears to be three-dimensional. In four-dimensional (4D) imaging systems, a series of three-dimensional images obtained at different times may be dynamically rendered to produce a moving 3D image, for example a 3D ultrasound movie.

Lighting effects may be added to a 3D or 4D image such that a subject of the image appears to be illuminated from a given position and/or direction. In recent years, 3D and 4D medical images have been made more realistic through the use of advanced lighting techniques (referred to as global illumination, gradient free lighting, subsurface scattering or photon mapping) that simulate illumination with a more physically accurate model than was previously used. In global illumination, a lighting model may be used that includes both direct illumination by light coming directly from a light source and indirect illumination, for example illumination by light that has been scattered from another surface.

In some global illumination rendering methods, an image is rendering from a volumetric imaging data set using a two-pass method in which a first pass creates a light volume, and a second pass uses the light volume to render an image for display.

The first pass may comprise a traversal from the light source into the volumetric imaging data set, in which virtual light is cast into the volumetric imaging data set. The irradiance due to the light source may be determined at each of a large array of points in the volumetric image data set using absorptive properties assigned to the voxels in dependence on the voxel intensities. The irradiance values at the array of points may be stored as a light volume. The light volume may be stored in memory. The light volume may be independent of the viewpoint.

A second pass may comprise a traversal through the light volume from a virtual camera, using the light volume to provide global lighting information. Rays may be cast from the virtual camera (for example, one ray for each pixel of the resulting rendered image), and irradiances from points along each ray may be integrated to provide pixel color values for a final rendered image.

Global illumination (GI) is gaining in popularity and may be considered to be ubiquitous in ultrasound. Global illumination may previously have been considered to occupy a niche in obstetrics, but now is used in a wide range of applications. For example, global illumination may be used in cardiac, radiology or vascular imaging. Global illumination may be used in three-dimensional Doppler imaging. There is also interest in the use of global illumination in other modalities, for example CT (computed tomography) and MR (magnetic resonance) imaging.

There is interest in using global illumination in a wide range of applications, including in virtual reality (VR). In VR, two views are rendered for each frame, with each view corresponding to a respective eye of a viewer. A viewpoint used to render the views is dependent on a head position of the viewer. The head position of the viewer will often move between frames.

In order to have a smooth appearance, a frame rate of 60 to 90 frames per second (fps) may be used for each of the views. The frame rate may be selected to result in a minimum delay. The frame rate may be selected to avoid lag that may occur when a displayed image does not keep up with a user's head movement.

A frame rate used for VR may be higher than a frame rate that may typically be used for four-dimensional imaging. For example, a moving image that is displayed on a screen may be displayed at a frame rate of 20 to 30 fps rather than the 60 to 90 fps frame rate that may be used for VR.

Due to the high frame rate, VR may be considered to be a demanding application with regard to rendering, and in particular with regard to global illumination. Determining complex light effects may require additional processing power when compared with simpler approaches to lighting.

In some circumstances, rendering of VR images using global illumination at a selected frame rate may be more than a single graphics processing unit (GPU) is capable of performing.

BRIEF DESCRIPTION OF THE DRAWINGS

Embodiments are now described, by way of non-limiting example, and are illustrated in the following figures, in which.

DETAILED DESCRIPTION

Certain embodiments provide a medical image processing apparatus for rendering medical images comprising a first GPU and a second GPU, each configured to read from and write to a data structure stored in virtual memory, wherein: the data structure is configured to be read by both the first GPU and the second GPU; the data structure is configured such that the first GPU can write to a first sub-space of the data structure and the second GPU can write to a second sub-space of the data structure; the first sub-space and the second sub-space are independent; the first GPU is configured to write data relating to pre-processing for rendering to the first sub-space; and the second GPU is configured to read the written data and to render at least one image based on the written data.

Certain embodiments provide a method for rendering medical images, comprising: reading, by each of a first GPU and a second GPU, respective data from a data structure stored in virtual memory; and writing, by each of a first GPU and a second GPU, respective data to the data structure, wherein: the data structure is configured to be read by both the first GPU and the second GPU; the data structure is configured such that the first GPU can write to a first sub-space of the data structure and the second GPU can write to a second sub-space of the data structure; the first sub-space and the second sub-space are independent; the first GPU is configured to write data relating to pre-processing for rendering to the first sub-space; and the second GPU is configured to read the written data and to render at least one image based on the written data.

Certain embodiments provide a medical image processing apparatus for rendering medical images comprising a multi-kernel GPU configured to read from and write to a data structure stored in virtual memory, wherein: the data structure is configured to be read by a first kernel of the GPU and a second kernel of the GPU; the data structure is configured such that the first kernel can write to a first sub-space of the data structure and the second kernel can write to a second sub-space of the data structure; the first sub-space and the second sub-space are independent; the first kernel is configured to write data relating to pre-processing for rendering to the first sub-space; and the second kernel is configured to read the written data and to render at least one image based on the written data.

Figure 1:
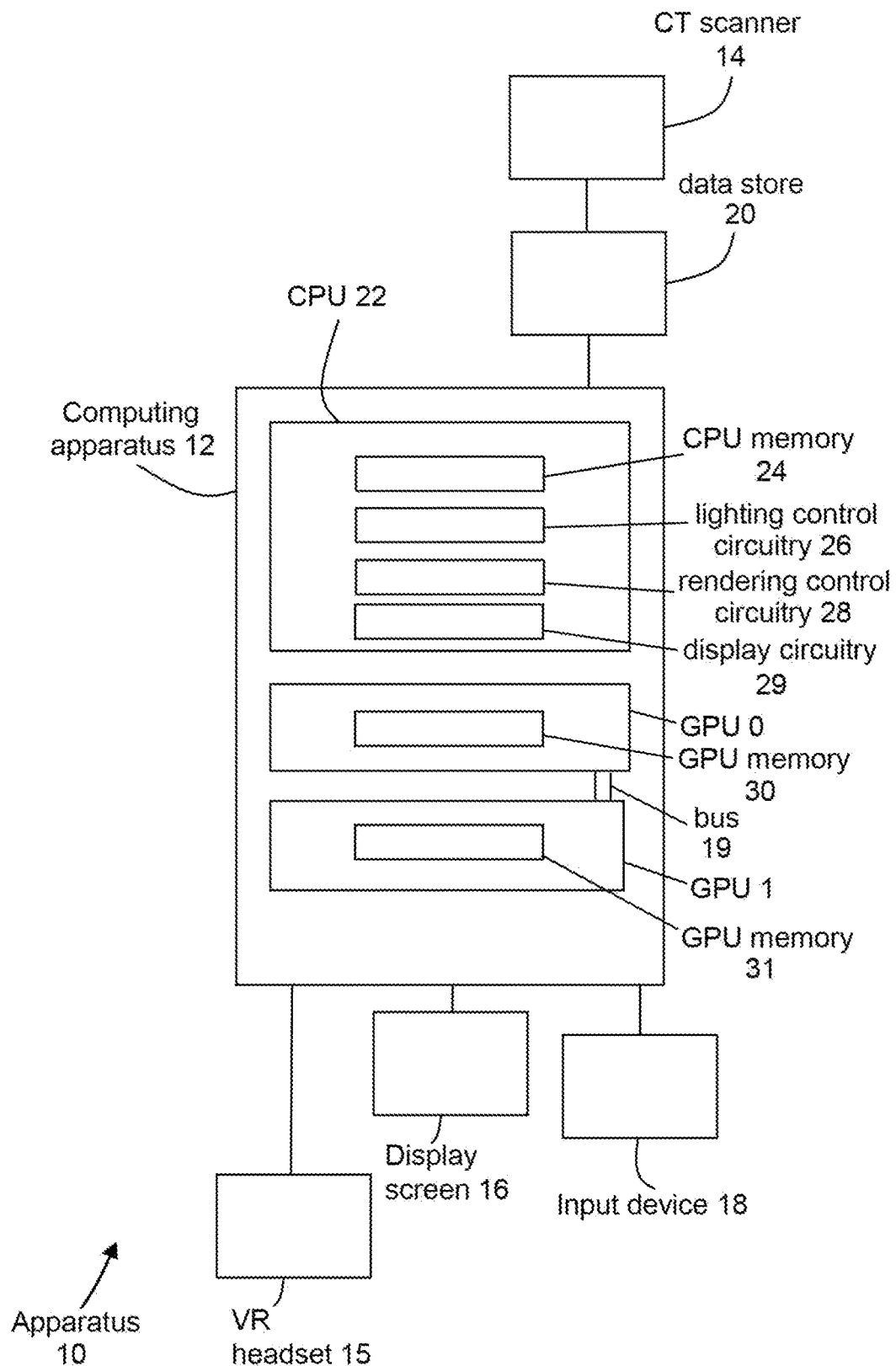
FIG. 1 is a schematic diagram of a medical imaging apparatus in accordance with an embodiment.

An apparatus 10 according to an embodiment is illustrated schematically in FIG. 1.

The apparatus 10 is configured to perform volume rendering of imaging data acquired by a medical imaging scanner 14 or scanners, which may comprise at least one of a CT (computed tomography) scanner, an MRI (magnetic resonance imaging) scanner, an X-ray scanner, a PET (positron emission tomography) scanner, a SPECT (single photon emission computed tomography) scanner, or an ultrasound scanner, or any suitable scanner. In the embodiment of FIG. 1, the rendering is of images for display on a VR headset 15.

The apparatus 10 comprises a computing apparatus 12, which in this case is a personal computer (PC) or workstation. In other embodiments, the computing apparatus 12 may be any suitable computing apparatus, for example a server, desktop computer, laptop computer, or mobile device. In further embodiments, functionality of the computing apparatus 12 may be provided by two or more computing apparatuses.

The computing apparatus 12 is connected to the scanner 14 or scanners via a data store 20.

The computing apparatus 12 is connected to the VR headset 15 and to a separate display screen 16. In other embodiments, any suitable display device or devices may be used in addition to, or instead of, the VR headset 15 and/or the display screen 16.

The computing apparatus is connected to an input device or devices 18, such as a computer keyboard, mouse or hand controller. In alternative embodiments, the display screen 16 is a touch screen, which also acts as an input device 18.

In the present embodiment, the computing apparatus 12 is configured to receive the medical imaging data that is to be processed from the data store 20. The data store 20 stores data acquired by the medical imaging scanner 14 or scanners.

In alternative embodiments, the computing apparatus 12 receives data from one or more further data stores (not shown) instead of or in addition to data store 20. For example, the computing apparatus 12 may receive data from one or more remote data stores (not shown) which may form part of a Picture Archiving and Communication System (PACS) or other information system, for example a laboratory data archive, an Electronic Medical Record (EMR) system, or an Admission Discharge and Transfer (ADT) system.

In further embodiments, the computing apparatus 12 is not connected to a scanner 14. The computing apparatus 12 may receive previously acquired medical imaging data from any suitable data store Computing apparatus 12 comprises a central processing unit (CPU) 22 and two graphics processing units (GPUs) GPU 0, GPU 1. In other embodiments, the computing apparatus 12 may comprise any suitable number of GPUs, for example three, four, five or six GPUs. The GPUs 0, 1 each comprise processing circuitry (not shown in FIG. 1) configured to perform image processing operations including lighting calculations and rendering calculations. The GPU 22 and GPUs together provide a processing resource for automatically or semi-automatically processing medical imaging data.

The CPU 22 comprises a memory 24, lighting control circuitry 26 for controlling lighting lighting calculation, rendering control circuitry 28 for controlling rendering, and display circuitry 29 for displaying rendered images on the VR headset 15. Circuitry of the CPU 22 may transfer data to and from the memory 24 via a memory bus (not shown), which may be configured to send data at a rate of, for example, around 100 GB/s. A memory controller (not shown) may be used to control reading data from the memory 24 and writing data to the memory 24. In other embodiments, the apparatus 10 may comprise multiple CPUs, each having a respective memory.

In the present embodiment, the circuitries 26, 28, 29 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays). In further embodiments, any suitable CPU components and/or GPU components may be implemented as one or more ASICs or FPGAs.

Each of the GPUs comprises respective GPU memory. GPU 0 comprises GPU memory 30 and GPU 1 comprises GPU memory 31. A bus 19 connects GPU 0 and GPU 1. For example, the bus 19 may be a 100 GB/s NVLink bus. The bus 19 facilitates data transfer between GPU 0 and GPU 1. In other embodiments, GPU 0 and GPU 1 may be connected in any suitable manner.

The GPUs 0, 1 are connected to the CPU 22 by a peripheral bus (not shown), for example a PCI-e bus. The peripheral bus may be configured to transfer data at, for example, around 10 to 64 GB/s. The peripheral bus may be a shared bus such that both GPUs 0, 1 communicate via the same bus and share the data transfer capacity of that shared bus.

The computing apparatus 12 also includes a hard drive and other components of a PC including RAM, ROM, one or more further data buses, an operating system including various device drivers, and hardware devices including a graphics card. Such components are not shown in FIG. 1 for clarity.

Figure 2:
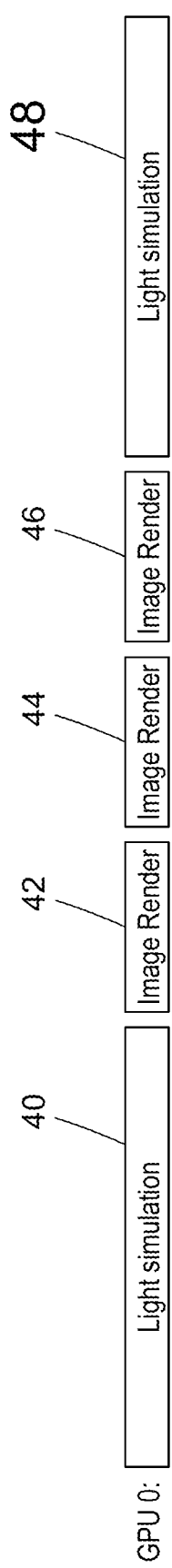
FIG. 2 is a schematic illustration of lighting and rendering processes performed by a single GPU.

FIG. 2 schematically illustrates an example of a rendering process that may be performed on a single GPU, for example GPU 0. In the rendering process of FIG. 2, lighting calculations are performed at a lower rate than rendering calculations.

At stage 40 of FIG. 2, the lighting control circuitry 26 instructs GPU 0 to perform a first light simulation on a volumetric imaging data set that is obtained from a medical imaging scan of a patient. The volumetric image data set comprises an array of voxels. The array of voxels is representative of a three-dimensional volume, which corresponds to some or all of the three-dimensional region of the patient. Each voxel has a position in the coordinate space of the volumetric imaging data set and an associated signal intensity.

The first light simulation of stage 40 simulates light from a plurality of virtual light sources. A position of each virtual light source is defined relative to a coordinate space of the volumetric imaging data set. In some embodiments, a position of one or more of the virtual light sources may be related to a position of the VR headset 15. For example, a virtual light source may be positioned such that it appears to be attached to a viewing point of the user of the headset. A position of the one or more light sources may be determined based on the position of the VR headset in any suitable manner.

In some embodiments, a position of one or more of the virtual light sources may be related to a position of a controller, for example a hand controller.

The first light simulation comprises casting rays from each light source through a volume of the volumetric imaging data set. Each simulated ray from the virtual light source distributes virtual light energy into the volume along the path of the ray. For each ray, irradiance due to the ray is calculated at each of a succession of sample points along the ray. The irradiance at each sample point is a product of the virtual light energy of the ray when it reaches the sample point and an absorption function at the sample point. Irradiance at the sample points is distributed to a plurality of neighboring voxels using any suitable method. The first light simulation may additionally simulate scattering and/or reflection as well as direct illumination.

An output of the first light simulation of stage 40 is an irradiance volume. The irradiance volume comprises a respective irradiance value for each of a set of voxels within the coordinate space of the volumetric imaging data set. The associated irradiance for each voxel may be a combination of irradiance contributions from a plurality of rays that have deposited virtual light energy at sample points near that point.

The irradiance volume is stored in a read write data structure 50. In the method of FIG. 2, the read write data structure 50 is implemented in a memory 30 of GPU 0.

At stage 42, the rendering control circuitry 28 instructs GPU 0 to perform a first image render using the volumetric imaging data set and the irradiance volume obtained at stage 40. A viewing position and orientation used in the first image render is determined based on a position of the VR headset 15 at a first time point. The position of the VR headset 15 may be determined in any suitable manner, for example by processing signals from a plurality of sensors positioned on the VR headset 15 and/or in the environment surrounding the VR headset 15.

The image is rendered as if viewed from each screen of the VR headset 15. The VR headset 15 has two screens, one corresponding to each eye of a wearer of the VR headset. Rays are cast into the volume represented by the volumetric imaging data set. Each ray may correspond to a pixel of a two-dimensional image data set that is to be obtained by the rendering. For a given ray that is cast from the camera, a value of irradiance is determined at each of a series of incremental points along the ray by reading interpolating irradiance from neighboring voxels of the irradiance volume. The irradiance values are obtained by reading data from the read write data structure 50.

Irradiances at each incremental point along a ray are integrated to obtain a pixel color value for the ray. The rendering control circuitry 28 thereby determines a color value for each pixel in a respective two-dimensional image data set for each screen of the VR headset 15.

An output of the first image render is a first pair of rendered images. Data representative of each of the rendered images is stored. The data representative of the rendered images is stored separately from the irradiance data and is not stored in the data structure 50. The display circuitry 29 instructs the rendered images to be displayed on the VR headset 15.

At stage 44, the rendering control circuitry 28 instructs GPU 0 to perform a second image render using the volumetric imaging data set and the irradiance volume obtained at stage 40. A viewing position and orientation used in the second image render is determined based on a position of the VR headset 15 at a second time point, which is later than the first time point. A viewing position and orientation may have changed between the first time point and the second time point, for example due to movement of the VR headset 15. Rendering is performed as described above with reference to stage 42. An output of the second image render is a second pair of rendered images, which are stored and are displayed on the VR headset 15 by the display circuitry 29.

At stage 46, the rendering control circuitry 28 instructs GPU 0 to perform a third image render using the volumetric imaging data set and the irradiance volume obtained at stage 40. A viewing position and orientation used in the third image render is determined based on a position of the VR headset 15 at a third time point, which is later than the second time point. A viewing position and orientation may have changed between the second time point and the third time point, for example due to movement of the VR headset 15. Rendering is performed as described above with reference to stage 42. An output of the third image render is a third pair of rendered images, which are stored and are displayed on the VR headset 15 by the display circuitry 29.

It is noted that the irradiance volume used does not change between the first image render and the third image render. A single light simulation process is used to provide lighting for multiple image renders.

At stage 48, the lighting control circuitry 46 instructs GPU 0 to perform a second light simulation on the volumetric imaging data set. Positions of virtual light sources may have moved between the first light simulation and the second light simulation. For example, virtual light sources may often be moved with the same interactivity as a view point, for example in accordance with movement of the VR headset 15. Positions of virtual light sources may be related to a hand controller. In other scenarios, virtual light sources may remain static but a volume may be moved.

An output of stage 48 is an updated irradiance volume. The updated irradiance volume is stored in the read write data structure 50. For example, the data of the updated irradiance volume may overwrite some or all of the data of the irradiance volume obtained at stage 40.

GPU 0 uses the updated irradiance volume to render subsequent frames (subsequent renders are not shown in FIG. 2). GPU 0 continues to alternate lighting and rendering calculations such that more rendering calculations than lighting calculations are performed. Lighting is updated at a lower rate than image rendering.

In general, it may be the case that a viewer would not notice that lighting is updated more slowly than image rendering. However, in the method of FIG. 2, the inclusion of lighting simulation stages causes a delay in image rendering, such that image rendering is not performed at a consistent frame rate. Image rendering may proceed at a steady rate while successive renders are performed. For example, a time interval between a time at which the second render is performed and a time at which the third render is performed may be the same as a time interval between a time at which the first render is performed and a time at which the second render is performed. However, after the third render, rendering is paused so that the GPU can perform lighting simulation. Latency may result. While the lighting simulation is being performed, image rendering may lag behind a current movement of the VR headset 15. It may not be possible for GPU 0 to provide image rendering at a desired frame rate (for example, 60 to 90 fps) when rendering is interspersed with light simulation stages.

Figure 3:
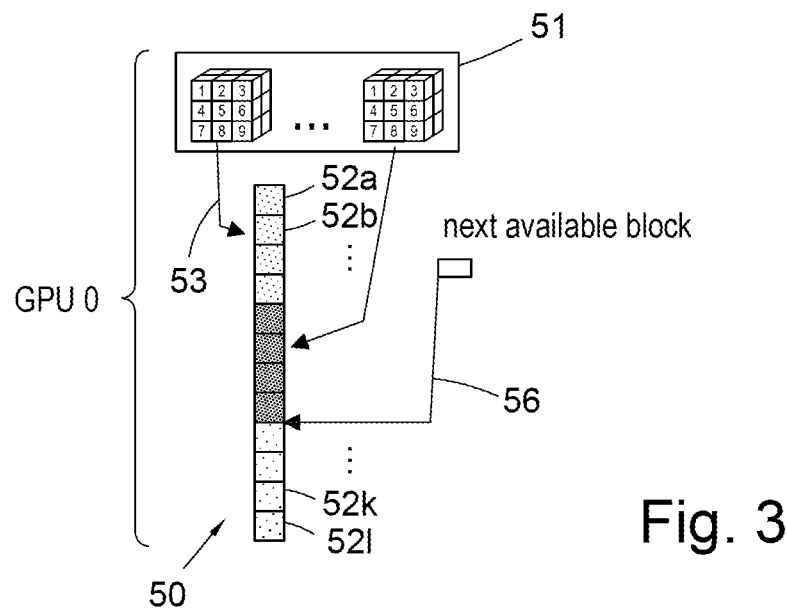
FIG. 3 is a schematic illustration of a data structure accessed by a single GPU.

FIG. 3 is a schematic illustration of a method of storing data volumes within a read write data structure 50, which may also be described as a light data heap 50. A single specific light data heap 50 comprises dynamic blocks 52a to 52l. Each block comprises multiple data values. For example, a block may be a block of 8×8×8 data values. In practice, the read write data structure 50 may comprise many more blocks than those shown in FIG. 3, which are reduced for simplicity.

An index structure 51 is a smaller volume containing integer indices referencing data in the main heap structure 50.

Data for a first volume is stored in blocks 52a to 52d of the data structure 50. A pointer 53 maps an index of the index structure 51 that is representative of a block of first volume to a corresponding block of the data structure 50. In practice, each block of the first volume may have a corresponding pointer providing a mapping from the index structure 51 to data in the data structure 50.

The data structure 50 may allow sparse data to be stored so that memory is used efficiently. For example, the data structure 50 may store only blocks that include relevant data. If multiple blocks of the first volume have the same data, that data may be stored in a single block of the data structure 50, with multiple pointers pointing to that one block. If a block of the first volume has no associated data, it may be compressed by using a null pointer.

Data for a second volume is stored in blocks 52e to 52h of the data structure 50. A pointer 55 maps an index of the index structure 51 that is representative of a block of the second volume to a corresponding block of the data structure 50. In practice, each block of the second volume that is stored in the data structure 50 may have a corresponding pointer providing a mapping from the index structure 51 to the data structure 50.

The index structure 51 lists the mappings between volumes and the blocks in which data for those volumes are stored. The volumes may be, for example, irradiance volumes or volumetric data sets.

A further pointer 56 shows the position of a next available block, which in the example shown is block 52i.

In the data structure 50 of FIG. 3, data for each of the volumes is stored in a contiguous set of blocks. The use of contiguous sets of blocks may assist in subsequent data processing.

GPU 0 is configured to read from data structure 50 and write to data structure 50 in a conventional manner. For example, GPU 0 may write data for an irradiance volume to the data structure 50 and then read the data for the irradiance volume when performing a subsequent rendering.

In FIG. 2, data (for example, irradiance data) is written to and read from a single data structure 50 such as that shown in FIG. 3. The data structure 50 is stored locally to GPU 0 in memory 30.

In general, global illumination algorithms make use of a simple read write data structure, for example a data structure as shown in FIG. 3. The use of such a data structure may make distribution of global illumination between multiple GPUs non-trivial. An algorithm for writing to, or reading from, the read write data structure may not automatically extend across GPUs.

Consider the apparatus 10 illustrated in FIG. 1. The CPU 22 has local memory 24. GPU 0 has local memory 30. GPU 1 has local memory 31. If excessive data transfer between the different local memories is required, delays may result. For example, if all data were to be duplicated such that a full set of data were to be held on both GPUs, repeated manual synchronization of the data may be required.

It is known to use virtual memory in which an address may refer to a location in any of a plurality of memories. For example, a virtual buffer of a virtual memory may include storage in CPU memory 24, storage in GPU memory 30, and storage in GPU memory 31. Addresses may point to locations in any one or more of CPU memory 24, GPU memory 30 and GPU memory 31. A pointer may be a one-to-many pointer that may point to any place within any of the memories 24, 30, 31 or to several places within the memories 24, 30, 31.

A naïve implementation of virtual memory to global illumination may result in an inefficient process with excessive transfers between the memories. For example, GPU 0 may try to access a given data item. If that data item is only stored a memory other than the memory 30 of GPU 0, the data item is duplicated from its storage location to GPU 0. Typically, the data item is duplicated as part of a larger data buffer. If an implementation of virtual memory includes a lot of instances in which data must be transferred the process may be slow, especially if the data transfer is over peripheral buses with limited data rates.

Figure 4:
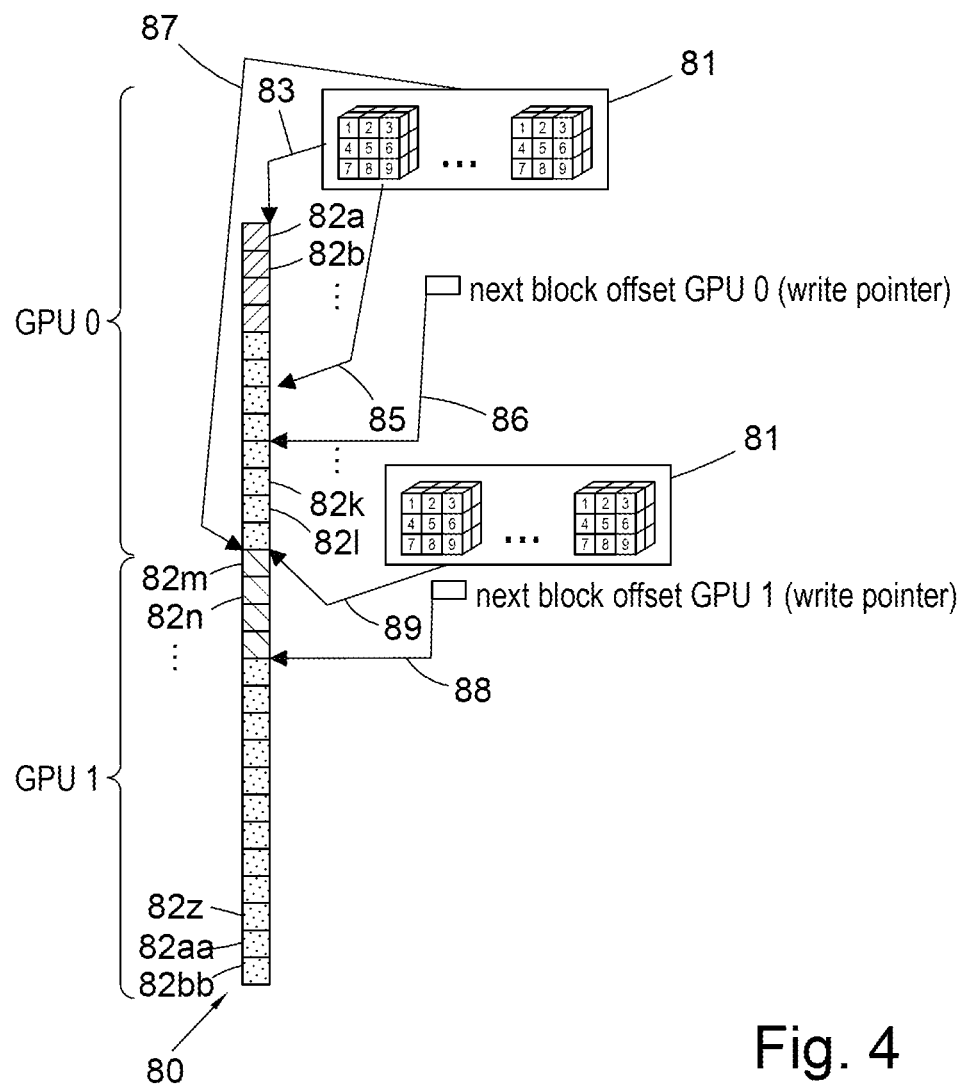
FIG. 4 is a schematic illustration of a data structure in accordance with an embodiments, wherein the data structure is accessed by at least two GPUs.

FIG. 4 is a schematic illustration of a method of storing data volumes within a read write data structure 80 in accordance with an embodiment. The data structure 80 is implemented as a single virtual buffer that uses memory of both GPU 0 and GPU 1.

The data structure 80 has a single set of addresses encompassing data stored in memory 30 of GPU 0 and data stored in memory 31 of GPU 1. The set of addresses may be referred to as a virtual address space or a virtual cross-GPU address space. Each GPU has a subset of the address space reserved for writing irradiance data. Only an index structure of the irradiance storage is explicitly synchronised between GPUs, leaving the irradiance data to be transferred as virtual memory pages as soon as they are available for transfer.

The data structure 80 segregates data so that data generated by GPU 0 is stored in a first sub-space of the virtual address space and data generated by GPU 1 is stored in a second sub-space of the virtual address space.

The data structure 80 comprises dynamic blocks 82a to 82bb. Each block comprises multiple data values. For example, a block may be a block of 8×8×8 data values. In practice, the data structure 80 may comprise many more blocks than those shown in FIG. 4, which are reduced for simplicity.

A first set of blocks 82a to 82l may be described as a first sub-space. A second set of blocks 82m to 82bb may be described as a second sub-space. Both GPU 0 and GPU 1 have read access to both the first sub-space and the second sub-space. However, only GPU 0 can write to the first sub-space, and only GPU 1 can write to the second sub-space. By segregating the blocks to which the different GPUs can write, unnecessary transfers of data may be avoided.

An index structure 81 is a smaller volume containing integer indices referencing data in the main heap structure 80.

Data for a first volume is stored in blocks 82a to 82d of the first sub-space. A pointer 83 maps an index of the index structure 81 that is representative of a block of the first volume to a corresponding block of the data structure 80. Data for a second volume is also stored in the first sub-space. Sparse data may be stored, for example as described above with reference to FIG. 3.

A light block mapping is private to GPU 0 but references unified memory. The index structure 51 lists the mappings between volumes and the blocks in which data for those volumes are stored. The volumes may be, for example, irradiance volumes or volumetric data sets. Data for each of the volumes is stored in a contiguous set of blocks. The use of contiguous sets of blocks may assist in subsequent data processing.

A pointer 86 shows the position of a next available block that is available to GPU 0. In the example shown, the next available block is block 82i. Pointer 86 may be referred to as a write pointer or heap write pointer. Pointer 86 points to a next block offset for GPU 0.

Turning to the second sub-space, data for a further volume is stored by GPU 1 in blocks 82m to 82p of the second sub-space.

A pointer 89 maps an index of the index structure 81 that is representative of a block of a third volume to a corresponding block of the data structure 80.

A pointer 88 shows the position of a next available block that is available to GPU 1. In the example shown, the next available block is block 82q. Pointer 88 may be referred to as a write pointer or heap write pointer. Pointer 88 points to a next block offset for GPU 1.

The first sub-space is exclusively written to by GPU 0 and the second sub-space is exclusively written to by GPU 1. Each GPU has its own heap write pointer 86, 88 showing the next available block to be written to by that GPU. When a GPU writes to the data structure 80, it only affects the position of its own heap write pointer. For example, when GPU 0 writes to the data structure 80, the position of heap write pointer 86 changes, but the position of heap write pointer 88 does not change. The heap write pointers 86, 88 may be considered to be parallel heap write pointers. The heap write pointer 86, 88 operate independently.

Independent regions are provided for each GPU in which that GPU has have exclusive write access. The full address range of the data structure 80 is accessible from both GPUs by page transfer, but write access is restricted. A unified memory page mapped area is provided. A single address range is used.

Each of GPU 0, GPU 1 has its own copy of the index structure 81. Data in the index structure 81 held at a given GPU is updated in response to actions performed by the GPU and by synchronization of the index structure with the index structure of the other GPU. In some embodiments, synchronization is performed in a single direction by sending index data from one GPU, for example GPU 1, to another GPU, for example GPU 0. In other embodiments, the synchronization may be bidirectional. For example, index data may be sent from GPU 0 to GPU 1, and further index data may be sent from GPU 1 to GPU 0.

Pages may be transferred either explicitly or automatically on access. For example, if a GPU tries to access data in the data structure 80 that is not available to it in its local memory, an automatic page transfer is initiated between the memory in which the data is held and the local memory. The transfer of pages is described further below with reference to FIGS. 6 and 7.

Figure 5:
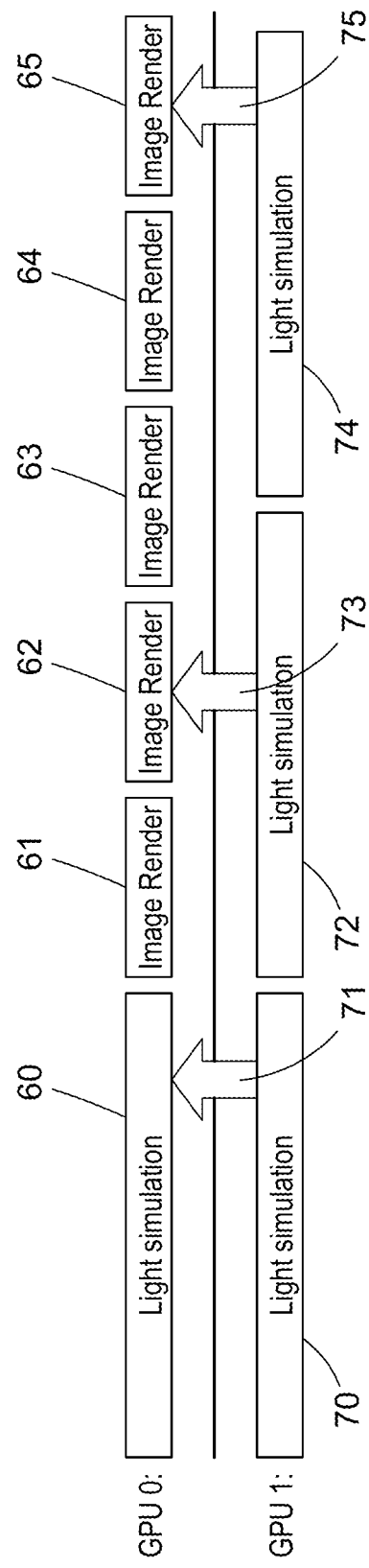
FIG. 5 is a schematic illustration of lighting and rendering processes performed by two GPUs in accordance with an embodiment.

FIG. 5 illustrates in overview a rendering method in accordance with an embodiment, which uses a data structure 80 as described above with reference to FIG. 4. A similar embodiment is described in greater detail below with reference to FIG. 6.

The method of FIG. 5 may be performed by the apparatus 10 of FIG. 1. In the rendering method of FIG. 5, rendering and lighting are assigned different GPUs and pipelined to run with minimal synchronization at independent rates. Lighting calculations may be performed at a lower rate than rendering calculations without causing uneven updates or lag. For example, lighting calculations may be updated at a frame rate of 20 to 30 fps while rendering calculations are updated at a frame rate of 60 to 90 fps.

A cooperative multi-GPU approach is used to allow a steady stream of both image data and light data. One dedicated rendering GPU (in this embodiment, GPU 0) produces images for the VR headset 15 while a separate GPU (in this embodiment, GPU 1) produces the lighting at a different rate. In other embodiments, any suitable number of GPUs may produce the images while a separate GPU or set of GPUs produces the lighting.

Both GPUs start by performing light simulation, since light simulation is required before rendering of images can commence.

At stage 60, lighting control circuitry 26 instructs GPU 0 to perform a first light simulation. GPU 0 performs the first light simulation on a volumetric imaging data set that is obtained from a medical imaging scan of a patient. The light simulation may also be referred to as a lighting simulation, light calculation, or lighting calculation. The light simulation may comprise a global illumination process. The light simulation may simulate any suitable number and/or type of virtual light sources. The light simulation may be similar to that described above with reference to FIG. 2. The process of light simulation may be described as a pre-processing step with respect to a subsequent rendering. In other embodiments, a similar method may be used with respect to any other suitable pre-processing step.

An output of the first light simulation of stage 60 is an irradiance volume. In the present embodiment, the light simulation process of stage 40 comprises photon mapping and the irradiance volume is a photon map. The photon map may be sparse. The photon map may not include individual irradiance values for every point within the coordinate space.

In other embodiments, the light simulation process comprises Montecarlo path tracing and an irradiance cache is stored. In further embodiments, a spatial data structure is used in which levels of the spatial data structure store individual irradiance queries. In other embodiments, regular light space mapping reads and writes dense volumes.

The irradiance volume is stored in a read write data structure 80 as described further below with reference to FIG. 5. The irradiance volume is stored in a first sub-space of the data structure 80 to which only GPU 0 has write access. The physical memory in which the irradiance volume is stored is memory 30 of GPU 0.

At stage 70, which may occur at least partially in a common time interval with stage 60, the lighting control circuitry 26 instructs GPU 1 to perform a second light simulation process. GPU 1 performs the second light simulation process on the same volumetric imaging data set as was used in stage 60. The second light simulation process may be performed using any suitable light simulation process. The second light simulation process may be used to simulate different light sources and/or different lighting effects to those simulated in the first light simulation process of stage 60.

In the embodiment of FIG. 5, no useful light state is available at a time at which the method of FIG. 5 is started. Both GPUs 0, 1 therefore cooperate to simulate the lighting as quickly as possible. Subsequent lighting simulations that overlap with rendering stages are not cooperative but are instead executed on a single GPU.

An output of the second light simulation of stage 70 is an irradiance volume. The irradiance volume is stored in a second sub-space of the data structure 80 to which only GPU 1 has write access. The physical memory in which the irradiance volume is stored is the memory 31 of GPU 1.

GPU 1 passes at least part of the output of the light simulation of stage 70 to GPU 0 as shown by arrow 71. This transfer is described further below with reference to FIG. 6. The transfer may comprise transferring data from GPU 1 to GPU 0 via bus 19, so that data that was previously stored in memory 31 is now stored in memory 30. It is noted that a change in physical location of the data storage does not change a position of the data in the data structure 80. Any of the data of the data structure 80 may be stored in memory 30, in memory 31, or in both memory 30 and memory 31.

When any part of the data structure 80 is being read, that part of the data structure 80 is considered to be read-only for the duration of the reading.

At stage 61, the rendering control circuitry 28 instructs GPU 0 to perform a first image render. GPU 0 performs the first image render using an irradiance volume obtained using data from the first light simulation process of stage 60 and from the second light simulation of stage 70. Any suitable rendering method may be used, for example a ray-casting method as described above with reference to stage 42. The first image render results in a first pair of rendered images. The display circuitry 29 instructs display of the first pair of rendered images on VR headset 15.

At stage 62, the rendering control circuitry 28 instructs GPU 0 to perform a second image render. GPU 0 performs the second image render using the same irradiance volume that was used for stage 61. The second image render results in a second pair of rendered images. The display circuitry 29 instructs display of the second pair of rendered images on VR headset 15.

At stage 72, the lighting control circuitry 26 instructs GPU 1 to perform a third light simulation process. GPU 1 performs the third light simulation process on the volumetric imaging data set. The third light simulation process takes a longer time to perform than an image render. An output of the third light simulation of stage 72 is an updated irradiance volume. The updated irradiance volume is stored in the second sub-space of the data structure 80, to which only GPU 1 has write access. GPU 1 transfers at least part of the output of the third light simulation process to GPU 0 via bus 19 (transfer shown as arrow 73) while the second image render 62 is being performed.

At stage 63, the rendering control circuitry 28 instructs GPU 0 to perform a third image render. GPU 0 performs the third image render on the volumetric imaging data set using the updated irradiance volume of stage 73. The third image render results in a third pair of rendered images. The display circuitry 29 instructs display of the third pair of rendered images on VR headset 15.

At stage 64, the rendering control circuitry 28 instructs GPU 0 to perform a fourth image render. GPU 0 performs the fourth image render using the volumetric imaging data set and the updated irradiance volume of stage 73. The fourth image render results in a fourth pair of rendered images. The display circuitry 29 instructs display of the fourth pair of rendered images on VR headset 15.

At stage 65, the rendering control circuitry 28 instructs GPU 0 to perform a fifth image render GPU 0 performs the fifth image render using the volumetric imaging data set and the updated irradiance volume of stage 73. The fifth image render results in a fifth pair of rendered images. The display circuitry 29 instructs display of the fifth pair of rendered images on VR headset 15.

At stage 74, the lighting control circuitry 26 instructs GPU 1 to perform another light simulation process. GPU 1 performs the light simulation process of stage 74 during a time period in which the third, fourth and fifth image renders 63, 64, 65 are being performed by GPU 0. An output of the light simulation of stage 74 is another irradiance volume. The irradiance volume of stage 74 is stored in the second sub-space of the data structure 80, to which only GPU 1 has write access. GPU 1 transfers at least part of the output of the light simulation process of stage 74 to GPU 0 via bus 19 (transfer shown as arrow 75) while the fifth image render 65 is being performed.

GPU 0 then uses results of the light simulation of stage 74 to render further images (not shown in FIG. 4).

Figure 6:
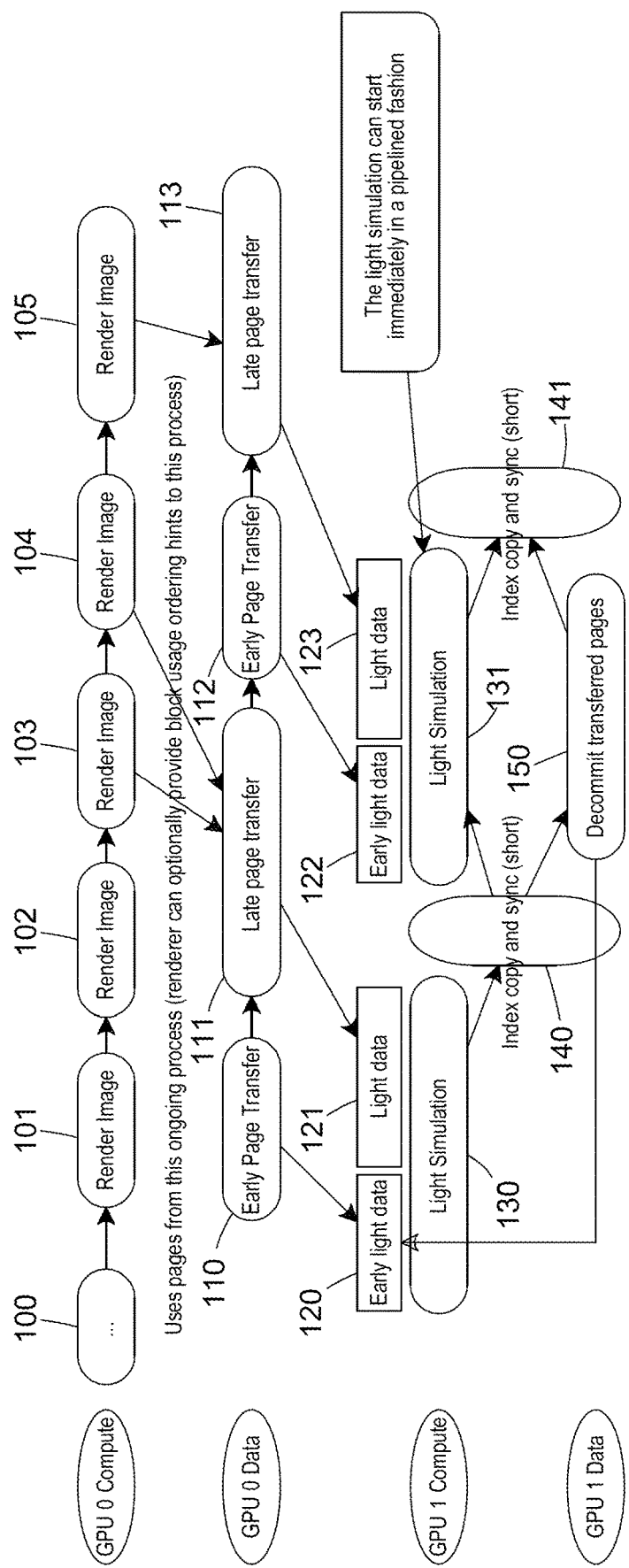
FIG. 6 is a flow chart illustrating in overview a method of an embodiment in which one GPU performs light simulation and another GPU renders images.

By performing light simulation on GPU 1 while rendering is performed on GPU 0, the light simulation may be updated without causing a lag in rendering. Light simulation may be performed at a slower frame rate than rendering. The use of a data structure 80 having separate sub-spaces for writing by GPU 0 and by GPU 1 may provide efficient data transfer between the GPUs. The data structure is accessed through a virtual memory system. FIG. 6 is a flow chart illustrating a process of light simulation and rendering similar to that described above with reference to FIG. 5, but showing data transfers in more detail.

FIG. 6 represents a plurality of steps performed by GPU 0 and GPU 1. A horizontal direction represents time from right to left. A top half of FIG. 6 represents steps performed by GPU 0. A bottom half of FIG. 6 represents steps performed by GPU 1.

Each GPU 0, 1 may be considered as having two threads operating at any given time. A first thread performs computation, for example computing a render or light simulation. The first thread is indicated in FIG. 6 as GPU 0

Compute and GPU 1 Compute. A second thread manages data. The second thread is indicated in FIG. 6 as GPU 0 Data and GPU 1 Data.

A first stage 100 of FIG. 6 represents renderings that have been performed previously to those shown explicitly in FIG. 6. FIG. 6 represents a period of time within an ongoing rendering process in which many frames are rendered in turn.

At stage 130, the lighting control circuitry 26 instructs GPU 1 to perform a light simulation. Although the light simulation is the first light simulation to be shown in FIG. 6, previous light simulations have been performed before the time period illustrated in FIG. 6. GPU 1 performs the light simulation. The light simulation of stage 130 results in early light data 120 followed by light data 121. The early light data 120 is a first portion of the data that is output by the light simulation of stage 130. The light data 121 is a second portion of the data that is output by the light simulation of stage 130. The early light data 120 and light data 120 are stored in the second sub-space of data structure 80, in memory 31.

At stage 101, the rendering control circuitry 28 instructs GPU 0 to render a pair of images. The image of stage 101 is referred to in the below discussion as a first pair of images. However, previous images have already been rendered by GPU 0 before the rendering of the first image. GPU 0 renders the first pair of images using irradiance data that has been obtained from a light simulation process that is not illustrated in FIG. 6. The rendering of the first image by GPU 0 takes place during a time period in which GPU 1 is performing the light simulation of stage 130.

At stage 110, GPU 0 requests a first page transfer from GPU 1. The first page transfer may be referred to as an early page transfer. In the early page transfer, the early light data 120 is transferred from GPU 1 to GPU 0, and is stored in memory 30. The early page transfer of stage 110 is performed at substantially the same time as the rendering of stage 101. The early page transfer of stage 110 is performed before the light simulation of stage 130 is completed.

At stage 111, GPU 0 requests a second page transfer from GPU 1. The second page transfer may be referred to as a late page transfer. In the late page transfer, the light data 121 is transferred from GPU 1 to GPU 0, and is stored in memory 30.

In FIG. 6, the data from the light simulation of stage 130 is divided into two portions 120, 121 which are transferred in two page transfers. In practice, data from a light simulation may be divided into any suitable number of portions which may be transferred in any suitable number of page transfers. The page transfers performed by GPU 0 all comprise page caching commands.

A rendering or merge process may keep a list of a block access order in order to efficiently overlap the transfer with the rendering or merge process. This may be measured from previous frames. The rendering or merge process may mark an elapsed frame duration when the block was first accessed. The elapsed frame duration may then be used to sort the blocks into a list of blocks in access order.

Blocks may be transferred just in time during the light simulation by observing the heap pointer from a second management thread. For example, the heap pointer may indicate which blocks have been started. An additional variable may indicate if each block is complete, as no additional light rays will intersect the block. The second management thread may scan the blocks that have been started looking for a finished status and then transfer those blocks that are marked as finished. In some circumstances, very limited synchronization may be needed in order to perform such a transfer. The transfer may require atomic access to the block heap pointer indicating the range of active blocks, and a flag that is used to signal a block's completion.

At stage 102, the rendering control circuitry 28 instructs GPU 0 to render a second pair of images. At the time at which GPU 0 performs the rendering of the second pair of images, data from the light simulation of stage 130 is not yet available to GPU 0. GPU 0 renders the second image using irradiance data that has been obtained from a light simulation process that is not illustrated in FIG. 6.

At stage 103, the rendering control circuitry 28 instructs GPU 0 to render a third pair of images. GPU 0 renders the third pair of images using a set of irradiance data obtained in the page transfers of stages 110 and 111.

At stage 104, the rendering control circuitry 28 instructs GPU 0 to renders a fourth pair of images. GPU 0 renders the fourth pair of images using the set of irradiance data obtained in the page transfers of stages 110 and 111.

Turning again to GPU 1, at stage 140 GPU 1 performs an indexing process in which a an index structure is copied and synchronized between the two GPUs 0, 1. In the present embodiment, index data of the index structure of GPU 1 is sent to GPU 0. The index structure comprises a mapping of data to memory locations. The copying may be described as a manual copy. In a manual copy, circuitry of the CPU directly instructs the GPU to immediately transfer a memory region without relying on a virtual memory or paging system. The synchronization of the index structure after the light simulation may be considered to be a key synchronization point.

At stage 150, GPU 1 decommits pages that have been transferred, which releases physical memory associated with the transferred pages.

At stage 131, the lighting control circuitry 26 instructs GPU 1 to performs a further light simulation. The further light simulation of stage 131 may start immediately after the light simulation of stage 130 in a pipelined fashion.

The further light simulation 131 results in early light data 122 followed by light data 123. The early light data 122 is a first portion of the data that is output by the light simulation 131. The light data 123 is a second portion of the data that is output by the further light simulation 131. The early light data 122 and light data 123 are stored in data structure 80, in memory 31.

At stage 112, GPU 0 requests a first page transfer from GPU 1, which may be referred to as an early page transfer. In the early page transfer, the early light data 122 is transferred from GPU 1 to GPU 0 and is stored in memory 30. A time period in which the early page transfer of stage 112 is performed overlaps with the rendering of the fourth image at stage 104. The early page transfer of stage 112 is performed before the further light simulation of stage 131 is completed.

At stage 113, GPU 0 requests a second page transfer from GPU 1, which may be referred to as a late page transfer. In the late page transfer, the light data 123 is transferred from GPU 1 to GPU 0 and is stored in memory 30.

Stage 141 occurs after the further light simulation 131 is complete. At stage 141, GPU 1 performs an indexing process in which a copy of an index mapping data to memory locations is copied and synchronized between the two GPUs 0, 1.

At stage 105, the rendering control circuitry 28 instructs GPU 0 to render a fifth pair of images using a set of irradiance data obtained in the page transfers of stages 112 and 113.

In the embodiment of FIG. 6, light simulation is performed by GPU 1 while rendering is performed by GPU 0. Unlike in the process shown in FIG. 2, the rendering is not delayed while light simulation is performed. Rendering proceeds at a consistent frame rate. Light simulation also proceeds at a consistent frame rate, which is lower than the frame rate used for rendering. Data is automatically transferred from GPU 1 to GPU 0 as it becomes available.

Processes transferring light information between GPU 0 and GPU 1 overlap with the light computation performed by GPU 1 as well as with the rendering call using the light information.

The data structure may appear unified and unmodified with transfers. The data structure may appear to exist in its entirety on both GPUs even if not quite all the data is common to both GPUs. Automatic page transfers are used to make parts of the data structure accessible from the required GPU. It may be considered that transfers do not change the information content itself, but only change the availability of the information content to each GPU. New lighting simulation results in modification of the content of the data structure, which may then be transferred between GPUs.

The method of FIG. 6 may be said to provide a method of cooperative irradiance storage. Writes are segregated by GPU. By segregating writes by GPU, unnecessary read/write stages may be avoided. Transfer of data between the GPUs may be minimized. Light simulation and rendering may be effectively performed within the constraint of a 100 GB/s data transfer capacity between the GPUs.

In many cases, it may be more cost effective to run a rendering process on multiple GPUs than on a single high performance GPU. By using the data structure 80, efficient multi-GPU performance may be achieved.

Rendering is performed at a steady rate which is different from a lighting calculation. By using a data structure as described above with reference to FIG. 4, transfers may be overlapped efficiently with minimal impact on the contents of the data structure.

It is not necessary to wait to transfers to complete before other actions are performed. If a GPU is performing a calculation that requires data that it does not have, it will automatically request the data from the other GPU. The automatic data transfers described with relation to FIG. 6 are designed to minimize inter GPU page faults, but it is possible for some page faults to occur without significantly disrupting the rendering method.

Efficient caching of pages may allow a useful rendering speed to be obtained. The data structure has an opportunity to synchronize light block mapping and commence a background transfer of pages between GPUs. Overlapping transfers are performed. Transfers may typically be performed before the data transferred is needed by the rendering engine, thereby keeping the rendering engine busy.

The method of FIG. 5 and FIG. 6 may also be extended to more than two GPUs. The data structure used may comprise more than two sub-spaces, such that the number of sub-spaces is the same as the number of GPUs. Each GPU is capable of reading any part of the data structure, but writes only to its dedicated sub-space. Each sub-space has a respective heap pointer showing a next available block.

Figure 7:
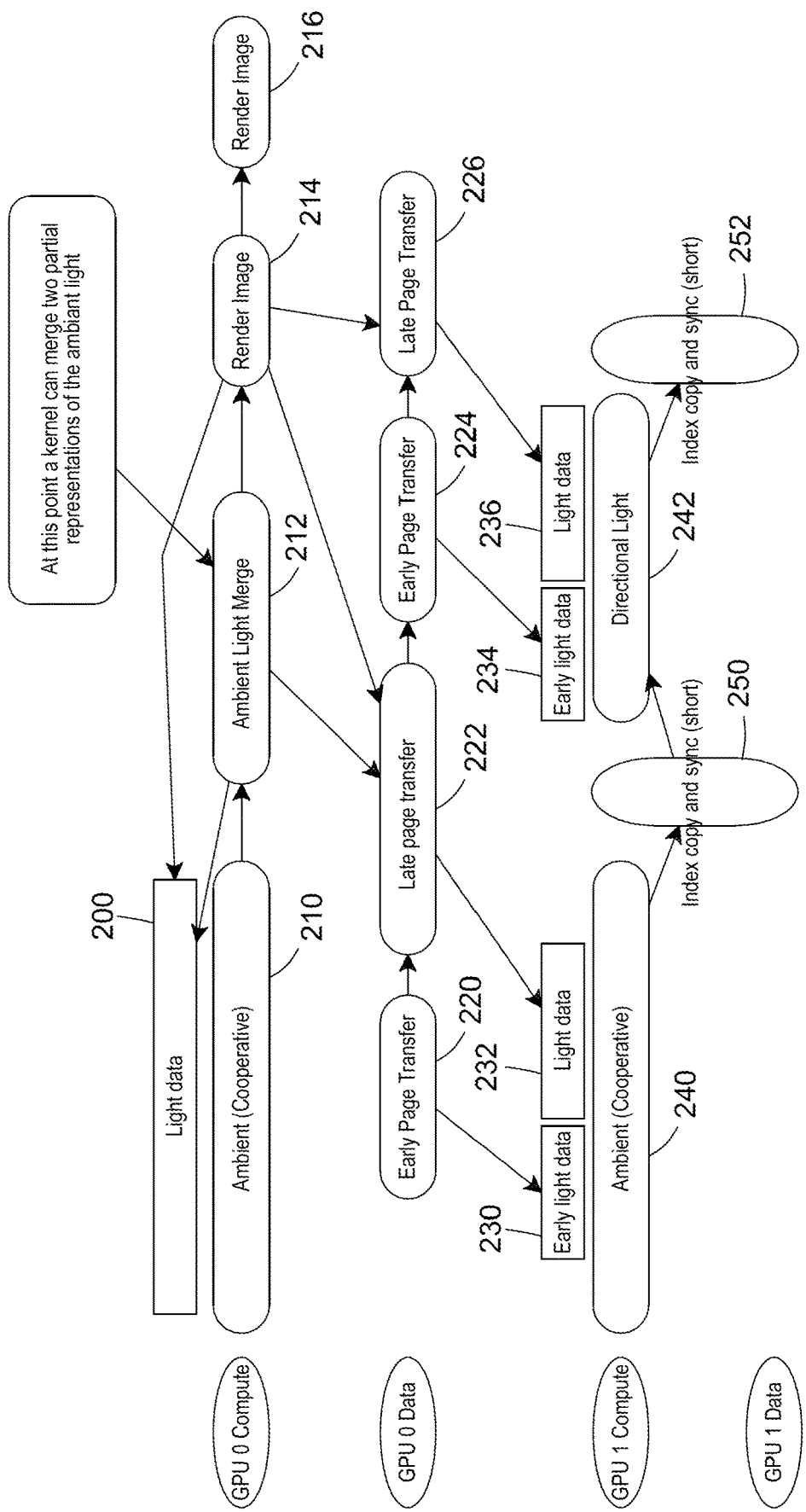
FIG. 7 is a flow chart illustrating in overview a method of an embodiment in which a lighting calculation is shared across two GPUs.

FIG. 7 is a flow chart illustrating a process of light simulation and rendering. In the method illustrated in FIG. 7, a cooperative lighting calculation is performed in which a lighting calculation is shared across GPU 0 and GPU 1. An expensive light calculation (which is ambient light in the embodiment of FIG. 7) is progressed on both GPU 0 and GPU 1, silently transferred and merged. While the transfer and merge is occurring, other lighting processes are performed for a current or next frame.

FIG. 7 represents a plurality of steps performed by GPU 0 and GPU 1. A horizontal direction represents time from right to left. A top half of FIG. 7 represents steps performed by GPU 0, separated into a first thread indicated as GPU 0 Compute and a second thread indicated as GPU 0 Data. A bottom half of FIG. 7 represents steps performed by GPU 1, separated into a first thread indicated as GPU 1 Compute and a second thread indicated as GPU 1 Data.

Stage 210 and 240 are performed at the same or overlapping times. At stage 210, the lighting control circuitry 26 instructs GPU 0 to perform a first ambient light calculation. At stage 240, the lighting control circuitry 26 instructs GPU 1 to perform a second ambient light calculation. The calculation of ambient light by GPU 0 and GPU 1 is cooperative. For example, the calculation may be divided by hemisphere such that GPU 0 performs calculation of ambient light for a first hemisphere and GPU 1 performs calculation of ambient light for a second hemisphere.

The calculation of ambient light by GPU 0 results in a set of light data 200 which is stored in data structure 80, in memory 30. The calculation of ambient light by GPU 1 results first in early light data 230 and then light data 232, which are stored in data structure 80, in memory 31.

Stage 250 occurs after stage 240 on GPU 1. At stage 250, GPU 1 performs an indexing process in which a copy of an index that maps data to memory locations is copied and synchronized between the two GPUs 0, 1.

At stage 220, GPU 0 performs an early page transfer. GPU 0 requests transfer of the early light data 230. The early light data 230 is transferred from GPU 1 to GPU 0 and stored in memory 30. At stage 222, GPU 0 performs a late page transfer 222. GPU 0 requests transfer of the light data 232. The light data 232 is transferred from GPU 1 to GPU 0 and stored in memory 30.

Stage 212 follows stage 210 on GPU 0. At stage 212, a kernel of GPU 0 performs an ambient light merge in which two partial representations of the ambient light are merged. The first partial representation is that obtained by GPU 0 at stage 210 and stored as light data 200. The second partial representation is that obtained by GPU 1 at stage 240 and transferred to GPU 0 in the early and late page transfers 220, 222. The merge makes use of the index synchronization of stage 240.

At stage 242, lighting control circuitry 26 instructs GPU 1 to perform a directional light calculation. Since the directional light calculation is less resource-intensive than the ambient light calculation, it is performed by one GPU rather than being split across both GPUs. The calculation of directional light by GPU 1 results first in early light data 234 and then light data 236. The early light data 234 and light data 236 are stored in data structure 80, in memory 31.

Stage 252 occurs after stage 242 on GPU 1. At stage 250, GPU 1 performs an indexing process in which a copy of an index that maps data to memory locations is copied and synchronized between the two GPUs 0, 1.

At stage 224, GPU 0 performs an early page transfer. GPU 0 requests transfer of the early light data 234. The early light data 234 is transferred from GPU 1 to GPU 0 and stored in memory 30. At stage 226, GPU 0 performs a late page transfer. GPU 0 requests transfer of the light data 236. The light data 236 is transferred from GPU 1 to GPU 0 and stored in memory 30.

At stage 214, the rendering control circuitry 28 instructs GPU 0 to perform a first image render. GPU 0 renders a first pair of images using light data 200, the results of the ambient light merge of stage 212, light data from the late page transfer of stage 222, and directional light data from the late page transfer of stage 226.

At stage 216, the rendering control circuitry 28 instructs GPU 0 to performs a second image render using the same light data as that used at stage 214. GPU 0 rendered a second pair of images using the same lighting information as was used at stage 214.

In the embodiment of FIG. 7, GPU 0 and GPU 1 cooperate on an expensive lighting calculation. By cooperating on an expensive light calculation, a time to image may be reduced in cases where independent lighting or rendering is sub-optimal.

A lighting calculation is divided into parts. Completed pages are transferred in an overlapping and just in time fashion, to then be merged.

Each GPU is able to contribute to both the task of lighting and the task of rendering (image production) as required.

In some embodiments, a shared multi-GPU accelerator is used for artificial intelligence (AI) and reconstruction. The shared multi-GPU accelerator may also be used to enable a fast GI experience. In some circumstances, other tasks may be running on the system and the algorithm that allocates lighting and rendering tasks on the GPUs may have to dynamically schedule tasks and subsequent data transfers to make way for such other tasks.

Figure 8:
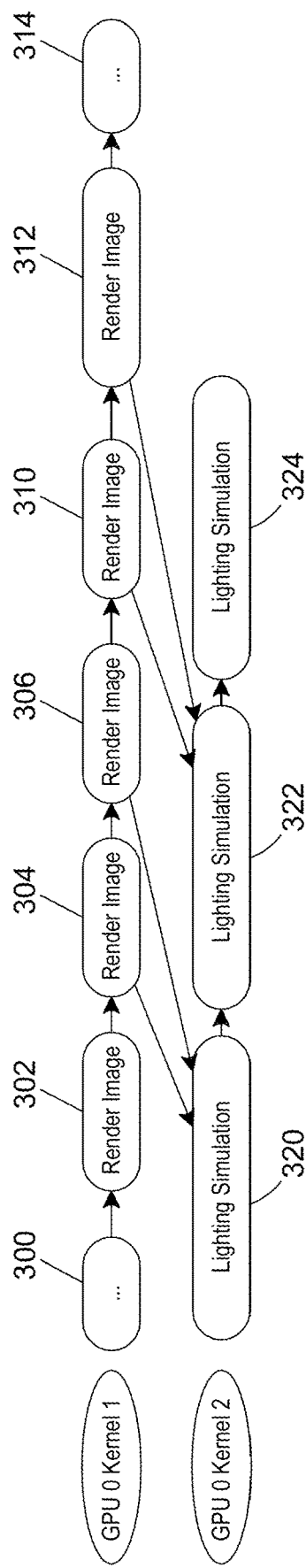
FIG. 8 is a flow chart illustrating in overview a method of an embodiment in which rendering is performed by a first kernel of a GPU and light simulation is performed by a second kernel of the same GPU.

FIG. 8 is a flow chart illustrating a process performed more than one kernel on a single GPU. In other embodiments, any of the methods described above as being performed on multiple GPUs may be performed on a single GPU with multi-kernel execution support.

In recent GPUs with simultaneous multi-threading, tasks may be overlapped within a single GPU.

In FIG. 8, a first kernel of GPU 0 is indicated as GPU 0 Kernel 1 and a second kernel of GPU 0 is indicated as GPU 0 Kernel 2.

The first kernel performs a number of previous rendering stages before the time period illustrated in FIG. 8, with these previous rendering stages being shown as stage 300. The first kernel then performs a plurality of rendering stages 302, 304, 306, 308, 310 as illustrated in FIG. 8. Rendering stages subsequent to the time period shown in FIG. 8 are shown as stage 312.

The second kernel performs three light simulations 320, 322, 324 during the period illustrated in FIG. 8.

The first image render 302 of FIG. 8 uses results of a previous light simulation (not shown). The second image render 304 and third image render 306 each use results of the first light simulation 320. The fourth image render 308 and fifth image render 310 each use results of the second light simulation 322.

In the method of FIG. 8, lighting and the rendering executes in parallel in a pipeline fashion with the rendering using the last completed result.

An operation that lowers latency may be favored when assigning operations to the kernels. In the case of rendering and light simulation, the operation that lowers latency may typically be rendering.

A priority of execution may be weighting by a time since the last lighting update. A weighting may be used to determine which operation to is be performed, for example lighting calculation versus rendering. The weighting may be dependent on how long it has been since a last lighting state was calculated, which may be described as a staleness of a lighting state. The weighting may be dependent on a latency of a produced rendering. The weighting may balance staleness of lighting state versus latency of the produced rendering. A target image frame rate and a target lighting frame rate can be used to drive the weighting scheme.

A benefit may still be obtained from pipelining as long as sufficient memory is available.

Pipelining may comprise the dividing up of a serial process into steps, each taking up a portion of the time taken for the full serial process. The process may work on multiple instances at a time even if the capacity at each step is limited to one item. For example, a next lighting simulation may be started while the result of a previous lighting simulation is still used by a current rendering process. Pipelining may reduce in a speeding up of the process.

In further embodiments, multiple GPUs that are each capable of multi-threading may be used.

In embodiments described above, the volumetric data set from which images are being rendered is a static data set that does not change during the rendering of successive images. For example, the volumetric data set may be a medical image data set that has been previously obtained by a medical scan. The VR headset may be used to fly through the scanned anatomy. In other embodiments, the volumetric data set may change while the rendering is being performed. Different rendering steps may be performed using different volumetric data. In such embodiments, the lighting calculation may be automatically restarted when the volumetric data set is changed. Both or all GPUs may be used to calculate a new lighting state before rendering restarts.

Embodiments above are described in relation to virtual reality, since virtual reality is an application that uses a particularly high frame rate. In other embodiments, images may be rendered for display on any suitable display device, which may not be a VR headset. Images may be rendered at any suitable frame rate.

Although the embodiments above are described with regard to medical imaging data, in other embodiments any data may be rendered using methods described above. For example, the data may comprise oil and gas data. The data may comprise three-dimensional microscopy data. The data may comprise, for example, climate data, geological surveys, demographics or games data.

Certain embodiments provide a medical image processing apparatus for rendering medical image comprising a first GPU, a second GPU, and a unified memory, wherein the unified memory configured to: be read by both of the first GPU and the second GPU, and, have a first sub-space which can be written by the first GPU and a second sub-space which can be written by the second GPU, wherein the first sub-space and the second sub-space are independent in each, and, the first GPU configured to write data relating to pre-processing for rendering to the first sub-space, and, the second GPU configured, to read the written data, and, to render image based on the written data.

Certain embodiments provide a medical imaging method in which: a single irradiance storage data structure spans a virtual cross GPU address space; each GPU gets a subset of that address space reserved for writing irradiance data; the method comprising a set of light simulation methods and/or rendering methods in which only the index structure of the irradiance storage is explicitly synchronized between GPUs leaving the irradiance data to be transferred as virtual memory pages as soon as they are available for transfer.

The rendering and lighting may be assigned different GPU and pipelined to run with minimal synchronization at independent rates.

A lighting work may be divided in parts. Completed pages may be transferred in an overlapping and just in time fashion, to then be merged in a kernel on a single GPU.

The irradiance structure may be a photon map, a spatial tree of irradiance queries (aka irradiance cache), or a dense volume.

A rendering/merge process may keep a list of the block access order in order to efficiently overlap the transfer with the rendering/merge process.

The cooperative multi-GPU rendering method may be used to drive a VR headset. One GPU may be tasked at ensuring user movement responsiveness.

The second GPU may be a SoC built-in GPU accessing system memory and communicating over PCIe.

An inter GPU link such as NVLink may be used to transfer pages.

Blocks may be transferred just in time during the light simulation by observing the heap pointer from a second management thread.

A shared multi-GPU accelerator, used for AI and reconstruction, may also be used to enable a fast GI experience.

In certain embodiments, there is provided a medical imaging apparatus comprising:

a single GPU with multi-kernel execution support; an irradiance data structure in the form of a photon map or dense irradiance volume; and a multi-pass global illumination algorithm; in which both the lighting and the rendering executes in parallel in a pipeline fashion with the rendering using the last completed result.

A priority of the execution may be weighted by the time since last lighting update.

A target image frame rate and a target lighting frame rate may be used to drive the weighting scheme.

Certain embodiments provide an image rendering method that uses a plurality of GPUs to perform rendering and lighting processes, the method comprising: generating irradiance data and storing the irradiance data in a storage structure comprising a virtual address space; providing each GPU with access to a respective sub-space of the virtual address space; and synchronizing between the GPUs an index structure of the virtual address space; and performing the lighting and rendering processes using the plurality of GPUs.

The rendering process and the lighting process may be performed by a first of the GPUs and a second of the GPUs respectively.

The first GPU and the second GPU may be configured to run the rendering process and the lighting process at different, independent rates.

The method may further comprise transferring irradiance data as virtual memory pages in response to them being available for transfer.

The lighting process results may be divided between completed pages transferred in an overlapping and just in time fashion, to then be merged in a kernel on a single GPU.

The irradiance structure may be either a photon map, spatial tree of irradiance queries (aka irradiance cache), or a dense volume.

A block access order may be maintained.

The method may further comprise driving a VR headset, wherein at least one of the GPUs is tasked with ensuring user movement responsiveness.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus for rendering medical images comprising a first GPU and a second GPU, each configured to read from and write to a data structure stored in virtual memory, wherein:
   the data structure is configured to be read by both the first GPU and the second GPU;
   the data structure is configured such that the first GPU can write to a first sub-space of the data structure and the second GPU can write to a second sub-space of the data structure;
   the first sub-space and the second sub-space are independent;
   the first GPU is configured to write data relating to a global illumination lighting calculation to the first sub-space, the written data comprising irradiance data;
   the second GPU is configured to read the irradiance data and to render at least one image based on the irradiance data, and
   the first GPU is configured to perform the pre-processing at a first frame rate, and the second GPU is configured to perform the rendering at a second, faster frame rate.

2. An apparatus according to claim 1, wherein the data structure is configured such that the first GPU is not permitted to write to the second sub-space and the second GPU is not permitted to write to the first sub-space.

3. An apparatus according to claim 1, wherein the data structure is configured for storage of data in a physical memory of the first GPU and for storage of data in a physical memory of the second GPU.

4. An apparatus according to claim 1, wherein the data structure comprises a virtual address space, the first sub-space is a first sub-space of the virtual address space and the second sub-space is a second sub-space of the virtual address space.

5. An apparatus according to claim 4, wherein processing circuitry of the first GPU and the second GPU is configured to synchronize between the GPUs an index structure of the virtual address space.

6. An apparatus according to claim 1, wherein the lighting calculation process comprises global illumination.

7. An apparatus according to claim 1, wherein the irradiance data comprises or forms part of at least one of: a photon map, a spatial tree of irradiance queries, a dense volume.

8. An apparatus according to claim 1, wherein processing circuitry of the first GPU is configured to transfer written data from a memory of the first GPU to a memory of the second GPU as virtual pages.

9. An apparatus according to claim 8, wherein the processing circuitry of the first GPU is configured to transfer the written data in response to the written data becoming available for transfer.

10. An apparatus according to claim 1, wherein circuitry of the first GPU is configured to perform a first part of a lighting calculation and write results of the first part of the lighting calculation to the first sub-space; circuitry of the second GPU is configured to perform a second part of the lighting calculation and write results of the second part of the lighting calculation to the second sub-space; and either circuitry of the first GPU or circuitry of the second GPU is configured to merge results of the first part of the lighting calculation with results of the second part of the lighting calculation.

11. An apparatus according to claim 1, wherein a block access order is maintained when data is transferred to or from the data structure.

12. An apparatus according to claim 1, further comprising an inter GPU link connecting the first GPU and second GPU, wherein the first GPU is configured to send the written data to the second GPU via the inter GPU link.

13. An apparatus according to claim 1, wherein the rendering of the at least one image based on the written data comprises rendering images for display on a virtual reality (VR) headset.

14. An apparatus according to claim 1, further comprising at least one further GPU configured to read and write to the data structure, wherein the data structure is further configured to be read by the at least one further GPU, and the data structure is configured such that the at least one further GPU can write to at least one further sub-space of the data structure.

15. An apparatus according to claim 1, wherein the data comprises medical imaging data.

16. A method for rendering medical images, comprising:
reading, by each of a first GPU and a second GPU, respective data from a data structure stored in virtual memory; and
writing, by each of a first GPU and a second GPU, respective data to the data structure, wherein:
the data structure is configured to be read by both the first GPU and the second GPU;
the data structure is configured such that the first GPU can write to a first sub-space of the data structure and the second GPU can write to a second sub-space of the data structure;
the first sub-space and the second sub-space are independent;
the first GPU is configured to write data relating to a global illumination lighting calculation to the first sub-space, the written data comprising irradiance data;
the second GPU is configured to read the irradiance data and to render at least one image based on the irradiance data, and
the first GPU is configured to perform the pre-processing at a first frame rate, and the second GPU is configured to perform the rendering at a second, faster frame rate.

17. A medical image processing apparatus for rendering medical images comprising a multi-kernel GPU configured to read from and write to a data structure stored in virtual memory, wherein:
the data structure is configured to be read by a first kernel of the GPU and a second kernel of the GPU;
the data structure is configured such that the first kernel can write to a first sub-space of the data structure and the second kernel can write to a second sub-space of the data structure;
the first sub-space and the second sub-space are independent;
the first kernel is configured to write data relating a global illumination lighting calculation to the first sub-space, the written data comprising irradiance data;
the second kernel is configured to read the irradiance data and to render at least one image based on the irradiance data, and
and the first GPU is configured to perform the pre-processing at a first frame rate, and the second GPU is configured to perform the rendering at a second, faster frame rate.

18. An apparatus according to claim 17, wherein lighting calculations and rendering calculations are assigned to the first kernel and the second kernel using a weighting method that is based on a time since a last lighting calculation.

* * * * *